(12) United States Patent
Sambasivam et al.

(10) Patent No.: US 8,679,581 B2
(45) Date of Patent: Mar. 25, 2014

(54) AMPHIPHILIC SILICONE COPOLYMERS FOR PRESSURE SENSITIVE ADHESIVE APPLICATIONS

(75) Inventors: Mahesh Sambasivam, Skillman, NJ (US); James Crivello, Troy, NY (US)

(73) Assignee: Convatec Technologies, Inc., Las Vegas, NV (US)

( * ) Notice: Subject to any disclaimer, the term of this patent is extended or adjusted under 35 U.S.C. 154(b) by 29 days.

(21) Appl. No.: 13/382,219

(22) PCT Filed: Jul. 7, 2010

(86) PCT No.: PCT/US2010/041191
§ 371 (c)(1), (2), (4) Date: Jan. 4, 2012

(87) PCT Pub. No.: WO2011/005846
PCT Pub. Date: Jan. 13, 2011

(65) Prior Publication Data
US 2012/0108749 A1    May 3, 2012

Related U.S. Application Data

(60) Provisional application No. 61/228,023, filed on Jul. 23, 2009, provisional application No. 61/223,534, filed on Jul. 7, 2009.

(51) Int. Cl.
*B05D 5/10* (2006.01)
(52) U.S. Cl.
USPC ........ 427/208.4; 523/111; 525/100; 525/103; 525/474; 525/479
(58) Field of Classification Search
USPC ........ 427/208.4; 523/111; 525/474, 479, 100, 525/103
See application file for complete search history.

(56) References Cited

U.S. PATENT DOCUMENTS

| | | | | |
|---|---|---|---|---|
| 4,900,809 A | * | 2/1990 | Tazi et al. | 528/497 |
| 5,214,119 A | * | 5/1993 | Leihr et al. | 528/28 |
| 2006/0074208 A1 | * | 4/2006 | Laredo | 526/279 |
| 2006/0134177 A1 | * | 6/2006 | Liu et al. | 424/427 |

OTHER PUBLICATIONS

Erdodi et al, Ideal Tetrafunctional Amphiphilic PEC/PDMS Conetworks by a Dual-Purpose Extender/Crosslinker. I. Syntheis, J. Polym. Sci. Part A: Polym. Chem., 43, 4953-4964 (2005)).
Uyanik, et al., Synthesis and Characterization of Poly(dimethyl siloxane) Containing Poly(vinyl pyrrolidone) Block Copolymers J. Appl. Polym. Sci., 71, 1915-1922 (1999)).
Gravier, et al., Graft and block copolymers with polysiloxane and vinyl polymer segments, Silicon Chemistry, 1, 107-120 (2002).
Yilgor et al., Novel Triblock Siloxane Copolymers: Synthesis, Chrraracterization, and Their Use as Surface Modifying Additives, J. Plym. Sci. Part A: Polym. Chem., 27, 3673-3690 (1989).
Yildiz et al., Compressive Elastic Moduli of Poly(N-Isopropylacrylamide) Hydrogels Crosslined with Poly(Dimenthyl Siloxane), J. Polym. Sci. Part A: Polym. Chem., 27, 3673-3690 (1989).
Crivello et al., Polydiethylsiloxane—Vinyl Block Polymers. I. The Synthesis of Polydimethylsiloxane Macroinitiators COntaining Thermolyzable Bis(Silyl Pinacolate Groups in Their Backbones, J. Polym. Sci: Part A: Polymer Chemistry, vol. 24, 1197-1215 (1986).
ISR dated Sep. 1, 2010 (PCT/US10/41191).

* cited by examiner

*Primary Examiner* — Robert Jones, Jr.
(74) *Attorney, Agent, or Firm* — Wilson, Sonsini, Goodrich & Rosati (57) ABSTRACT

Silicone pressure sensitive adhesive compositions including amphiphilic copolymers. The amphiphilic copolymers are based on a polydimethylhydrogensiloxane or polydimethylsiloxane based macroinitiator. A medical device including said pressure sensitive adhesive compositions for securing the device to human skin or tissue.

6 Claims, 11 Drawing Sheets

AMPHIPHILIC SILICONE COPOLYMERS FOR PRESSURE SENSITIVE ADHESIVE APPLICATIONS

CROSS-REFERENCE

This application is filed pursuant to 35 U.S.C. §371 as a United States National Phase Application of International Application Ser. No. PCT/US10/41191, filed Jul. 7, 2010, which claims the benefit of and the right of priority to U.S. Provisional Application No. 61/228,023 filed Jul. 23, 2009 and 61/223,534 filed Jul. 7, 2009, which application is incorporated herein by reference.

BACKGROUND OF THE INVENTION

Silicone pressure sensitive adhesives are widely used in transdermal drug delivery, wound dressings, scar dressings, and other healthcare applications. These adhesives are typically a condensation product of silicate resin and polydimethylsiloxane (PDMS) fluid, or a reactive blend of vinyl- and hydride-containing PDMS and a silicate resin cured via hydrosilylation reaction (Dow Corning Literature, *Silicone Pressure Sensitive Adhesives* (2002)). These adhesives are biocompatible, gentle on the skin, and securely attach medical devices to the body when the environment is dry. However, under moist conditions such as during skin perspiration, the hydrophobic silicone adhesives lose their adhesion to skin, which can lead to the dressing detaching from the body prematurely.

There is a need to improve the adhesion of these adhesives to skin in the presence of moisture. Traditionally, adhesion under moist environment in skin adhesives have been accomplished by adding water absorbing fillers such as hydrocolloids to pressure sensitive adhesives. The hydrocolloid fillers absorb moisture and soften, providing wet tack, thereby improving the adhesion to skin longer. However, the disadvantages of this approach are the reduction in the dry peel strength and tack properties of the adhesive due to the presence of hard fillers. In addition, because of the affinity of the fillers for water, they dissolve and leach out of the adhesive, which can leave a slimy residue on the skin after the dressing removal.

In order to improve the adhesion of silicone adhesives under a moist environment and to overcome the drawbacks of previous approaches, the present approach is to add a suitable amphiphilic silicone copolymer to a silicone pressure sensitive adhesive. An ideal amphiphilic silicone copolymer suitable for such applications should possess high cohesive strength, high moisture vapor transmission rate (MVTR), high pressure sensitive adhesion to surfaces, maintain adhesion even under moist conditions, and should not leach out components or leave a residue. Commercially available amphiphilic silicone copolymers are typically based on grafted poly(ethylene glycol). These copolymers are low molecular weight liquids, which are typically used as surfactants or defoamers. Addition of such low molecular weight copolymers can affect the adhesive performance because of surface migration under moist conditions and lead to a reduction in adhesion.

Several amphiphilic silicone copolymers have been reported in the literature. Recently, G. Edrodi and J. P. Kennedy published the synthesis of amphiphilic conetworks of poly(ethylene glycol) (PEG) and polydimethylsiloxane (PDMS) (G. Edrodi and J. P. Kennedy, *J. Polym. Sci. Part A: Polym. Chem.*, 43, 4954-4963 (2005)). The amphiphilic conetworks exhibited swelling in water and hexane indicating bi-continuous phases.

Yildiz, et al. synthesized block copolymer of poly(vinyl pyrrolidone)-poly(dimethyl siloxane)-poly(vinyl pyrrolidone) (J. C. Kim, M. Song, S. Park, E. Lee, M. Rang, and H. Ahn, *J. Appl. Polym. Sci.*, 85, 2244-2253 (2002)). They prepared a di-isocyanate terminated PDMS which was then end-capped with t-butyl peroxide. This was used as a macroinitiator for N-vinyl pyrrolidone polymerization. The resulting copolymers showed lower glass transition temperature (Tg) than the homopolymer poly(vinyl pyrrolidone).

Graiver, et al. used aldehyde-functional silicones as reactive sites for vinyl copolymerization in the presence of a copper redox system (D. Graiver, G. T. Decker, Y. Kim, F. J. Hamilton, and H. J. Harwood, *Silicon Chemistry*, 1, 107-120 (2002)). Several graft and block copolymers including polymethacrylic acid and polyacrylic acid were incorporated into the silicone polymer. These polar segments were formed by the thermal decomposition of the t-butyl ester substituted polyacrylate segments.

Yilgor, et al. synthesized triblock copolymers of polycaprolactone-PDMS, and poly(2-ethyl-2-oxazoline)-PDMS (I. Yilgor, W. P. Steckle, E. Yilgor, R. G. Freelin, and J. S. Riffle, *J. Polym. Sci. Part A: Polym. Chem.*, 27, 3673-3690 (1989)). For the caprolactone, hydroxyl-terminated PDMS was used as a macroinitiator, and for the oxazoline copolymers, benzyl chloride-terminated PDMS was used. The resulting copolymers with a silicone content of about 30-50% were shown to reduce the surface tension of plastics, such as PET, PMMA, and polyurethane.

Yildiz, et al. synthesized poly(N-isopropylacrylamide) hydrogels using diacrylate-terminated PDMS as the crosslinker (Y. Yildiz, N. Uyanik, and C. Erbil, *J. Macromol. Sci., Part A: Pure and Applied Chemistry*, 43, 1091-1106 (2006)). The resulting hydrogels were found to have higher compression moduli compared to the conventional crosslinker, N,N'-methylene bis-acrylamide. This was attributed to the hydrophobic interactions between PDMS segments in the network.

DESCRIPTION OF THE DRAWINGS

Scheme 1 shows the synthetic scheme for an amphiphilic silicone block copolymer using a PDMS macroinitiator.

Scheme 2 shows the synthetic scheme for an amphiphilic silicone graft copolymer using a PDMS macroinitiator.

DESCRIPTION OF THE INVENTION

This invention relates to a pressure sensitive adhesive comprising one or more amphiphilic copolymers of polydimethylsiloxane, wherein the copolymer is prepared using a polydimethylsiloxane or polymethylhydrogensiloxane macroinitiator and at least one reactive hydrophilic or amphiphilic monomer, oligomer, macromer and combinations thereof. The reactive hydrophilic or amphiphilic monomer is selected from a group consisting of N-vinyl caprolactams, vinyl esters, vinyl ethers, unsaturated acids or anhydrides and their salts, acrylates, methacrylates, acrylamides, methacrylamides, N-alkyl acrylamides, cyanate esters, hydroxy-alkyl acrylamides, glycidyl esters, glycidyl ethers, allyl monomers, and combinations thereof.

The reactive hydrophilic or amphiphilic oligomer and macromer are selected from a group consisting of an polyalkyleneoxide, polyether, polyurethane, polyester, polyamide, polysaccharide, polypeptide, polyacrylate, polymethacrylate, polyacrylamide, with reactive groups selected from vinyl, epoxy, allyl, and combinations thereof.

A macroinitiator is a compound capable of initiating a polymerization reaction, wherein the molecular weight of the said compound is at least 200 g/mol.

Accordingly, the invention includes a pressure sensitive adhesive comprising one or more amphiphilic copolymers of poly(dimethylsiloxane)-poly(maleic anhydride-vinyl ethyl ether) (PDMS/MA/VEE) and a silicone gel adhesive blended together.

The invention further includes a medical device having a pressure sensitive adhesive comprising one or more amphiphilic copolymers of polydimethylsiloxane, wherein the copolymer is prepared using a polydimethylsiloxane or polymethylhydrogensiloxane macroinitiator and at least one reactive hydrophilic or amphiphilic monomer or oligomer or macromer. Examples of medical devices for which such an adhesive is applicable include ostomy devices, wound management devices, skin and incontinence care and infusion devices.

Synthesis of Polydimethylsiloxane-poly(maleic anhydride-alt-vinyl ethyl ether) (PDMS/MA/VEE):

The synthesis of the terpolymers were based on the copolymerization of maleic anhydride and vinyl ethyl ether (PDMS/MA/VEE) using a PDMS macrointiator (Scheme 1) according to the procedure described by Crivello et al. (J. V. Crivello, D. A. Conlon, and J. L. Lee, J. Polym. Sci. Part A: Polym. Chem., 24, 1197-1215 (1986)). The uniqueness of the present invention includes the incorporation of hydrophilic groups into a siloxane polymer which surprisingly yields a polymer additive suitable for pressure sensitive adhesives with desirable peel adhesion, moisture management and biocompatibility.

A reactive silicone, α,ω-hydride-terminated polydimethylsiloxane, DMS-H25, from Gelest, Inc., was used as a precursor to prepare the macroinitiator. This polymer is listed to have a molecular weight of 17,200 g/mol and about 0.01 mol % Si—H groups. Briefly, the macroinitiator was prepared by reacting bis(dimethylvinylsilyl)benzopinacolate with α,ω-hydride-terminated PDMS precursor in the presence of Karstedt's catalyst. For the terpolymer synthesis, about 2.0 g of the polydimethylsiloxane macroinitiator was mixed with an equimolar ratio of maleic anhydride and vinyl ethyl ether in a 150 mL of dried toluene in a 250 mL flask equipped with paddle stirrer, reflux condenser and nitrogen inlet. The macroinitiator to comonomer molar ratios (PDMS/MA/VEE) synthesized were 2/1/1 and 2/2/2. The polymerization was initiated by raising the temperature to 80° C. and the reaction was continued for 5 hours. At the end of the reaction, the terpolymer was precipitated with methanol, and dried at room temperature under vacuum. The polymerization yield was about 95% in both compositions. It should be noted that even though Scheme 1 shows a triblock structure, it is anticipated that there are diblocks and multiblocks also in the mixture.

Scheme 1 Silicone block copolymer synthesis

"PDMS/MA/VEE"

Reference: J. V. Crivello, D. A. Conlon, and J. L. Lee, J. Polym Sci. Part A: Polym Chem., 1197-1215 (1986)

Scheme II Silicone graft copolymer synthesis

A PDMS-hydride is reacted with an oxirane containing compound such as cyclohexene oxide (shown here as an example), glycidyl methyl ether, etc. to synthesize an amphiphilic PDMS copolymer Example Using Scheme I
PDMS/MA/VEE Terpolymer Characterization Solubility studies were carried out in deuterated methanol, 2-propanol, and toluene. In 2-propanol, and deuterated methanol, the terpolymer showed partial solubility but mainly remained as a suspension, and in toluene, it was insoluble. However, the terpolymers dissolved completely in toluene/2-propanol (1:1 ratio) mixture indicating the presence of both polar and non polar chain segments in the terpolymer. The terpolymer samples when immersed in dilute alkali solution showed some swelling.

Samples PDMS/MA/VEE 2/1/1 and PDMS/MA/VEE 2/2/2 were analyzed by $^1$H NMR. The terpolymers were dissolved in a mixture of in a 50:50 v/v mixture of non-deuterated 2-propanol and toluene-$d_8$ for analysis.

Thermogravimetric Analysis (TGA) was performed on the copolymer samples and the $\Omega,\omega$-hydride-terminated PDMS precursor (DMS-H25). The presence of any volatile fraction was analyzed as well as the degradation behavior of the terpolymer systems. All samples were run from 30° C. to 900° C. at 10° C./minute in air using sample weight ranging from 2 to 12 mg.

Differential Scanning calorimetry (DSC)—the PDMS/MA/VEE samples were dried in a vacuum oven overnight prior to testing. This was done due to the observed 4-10% weight loss on the TGA by these samples in the temperature range of the DSC run. Samples were analyzed by dual heat DSC in hermetic pans from −90° C. to 200° C. at 10° C./minute.

The samples were tested by Fourier transform infrared (FTIR) spectroscopy in attenuated total internal reflectance (ATR) mode.

Example Using Scheme II

Synthesis of poly(methylhydrogensiloxane)-co-PDMS-g-poly(cyclohexene oxide) (PMDS-g-CHO) and poly(methylhydrogensiloxane)-co-PDMS-g-poly(glycidyl methyl ether) (PMDS-g-CHO)

Graft Polymerization of Cyclohexene Oxide onto Poly(Methylhydrogen Siloxane)

The graft polymerization of cyclohexene oxide or glycidyl methyl ether onto poly(methylsiloxane) was carried out in toluene. Both the monomer and solvent were dried with calcium hydride. In a dry 250 mL flask equipped with magnetic stirrer and reflux condenser, 50 mL of dry toluene, 12 g (0.12 mol) of cyclohexene oxide or glycidyl methyl ether and 8.0 g of a Methylhydrosiloxane-dimethylsiloxane copolymers (HMS-064 from Gelest; molecular weight 55000-65000, Si—H: 5-7 mol %) were introduced under nitrogen atmosphere. After the dissolution, 0.627 g of the Ashby catalyst was added. The reaction was left for about 12 h at 25° C. At the end of this time, the graft copolymer was precipitated with methanol, and dried at room temperature under vacuum.

TABLE 1

| Copolymer | Grafted Copolymers | | Copolymer Type PDMS precursor | | Block Copolymers | | |
|---|---|---|---|---|---|---|---|
| | Methylhydrosiloxane-dimethylsiloxane copolymers HMS-064 MW: 55K-65K (from Gelest, Inc.) Si—H mol %: 5-7 | | Hydride terminated PDMS DMS-H25 MW: 17.2K (from Gelest Inc.) Si—H mol %: 0.01 | | | | |
| | PDMS/ CHO | PDMS/ GME | PDMS/ VP | PDMS/ VA/MA | PDMS/ VEE/MA | PDMS/ VPEG | PDMS/ DOM/VA |
| Material ratio | PDMS:CHO = 1:1, 1:1.5, 1:2(wt) | PDMS:GME = 1:1.5, 1:2.3, 1:4(wt) | PDMS:VP = 1:1.5, 1:2.3, 1:4(wt) | PDMS: (VA/MA) = 1:1.5, 1:2.3, 1:4(wt) | PDMS:VEE:MA = 2:1:1, 2:2:2(wt) | PDMS:VPEG = 1:1.5, 1:2.3, 1:4(wt) | PDMS:(DOM/ VA = 1/1 mol) = 1:1.5, 1:2.3, 1:4(wt) |
| Phenomenon | All three samples are soft, not sticky, no water swellability. | Microgel found using Undistilled GME. Using multistep-distilled GME (1. CaH2 and 2. triisobutyl aluminum, and vacuum distilled), only 1:4 sample is not gel. | VP washed and distilled. After reaction system separated into two phases for 1:2.3, 1:4, Clear solution for 1:1.5 | Precipitate during polymerization | Not swell in saline (0.9%) or DI water, but swell in alkali solution. | After polymerization, cloudy solution for 1:1.5, two phases for 1:2.3, white cream for 1:4 | After polymerization, clear solution for 1:1.5, 1:2.3, cloudy solution for 1:4 |
| Molecular weight | PDMS Mw: 97k, Mn: 44k PDMS/ CyHO(1/1): Mw: 234K, Mn: 106K, PDMS/ CyHO(1/1.5): Mw: 276K, Mn: 119K, PDMS/ CyHO(1/4): Mw: 338K, Mn: 132K, | PDMS: Mw: 210K, Mn: 93K. PDMS/GME (1/4): Mw: 830K, Mn: 250K. Solvent: THF/CHCl3 = 1/1 | No suitable solvent | PDMS:(VA/ MA)(1:4) Mw: 42K, Mn: 22K, (1:2.3) Mw: 43K, Mn: 23K, in THF/ CHCl3 = 1/1 | Toluene/IP A is good solvent, but no RI signals, probably due to close RI of solvent and polymer | PDMS 2H: Mw: 48K, Mn: 28K. PDMS 2H initiator ply: Mw: 51K, Mn: 17K. PDMS/VPEG (1/2.3): Mw: 64K, Mn: 40K, PDM/VPEG (1/4): Mw: 57K, Mn: 37K. In THF/CHCl3 (1/1) | PDMS 2H: (DOM/VA = 1/1 mol) 1/1.5: Mw: 57K, Mn: 34K. 1/2.3: Mw: 57K, Mn: 33K. 1/4: Mw = 54K, Mn = 33K. In THF/ CHCl3(1/1) |
| Appearance | Rubbery gel | Rubbery gel with some tack | 1:1.5 white glue, 1:2.3, 1:4 white powder | Clear liquid | White powder | White cream | Clear liquid |

Figure 1:
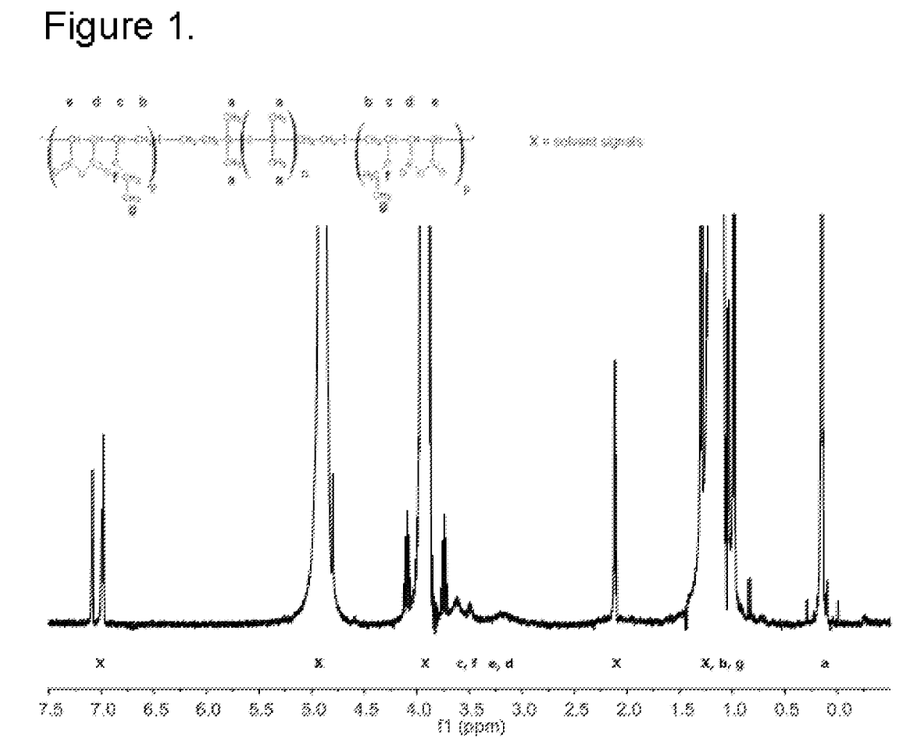
FIG. 1 shows the $^1$H NMR spectrum of PDMS/MA/VEE 2/1/1 terpolymer.
Figure 2:
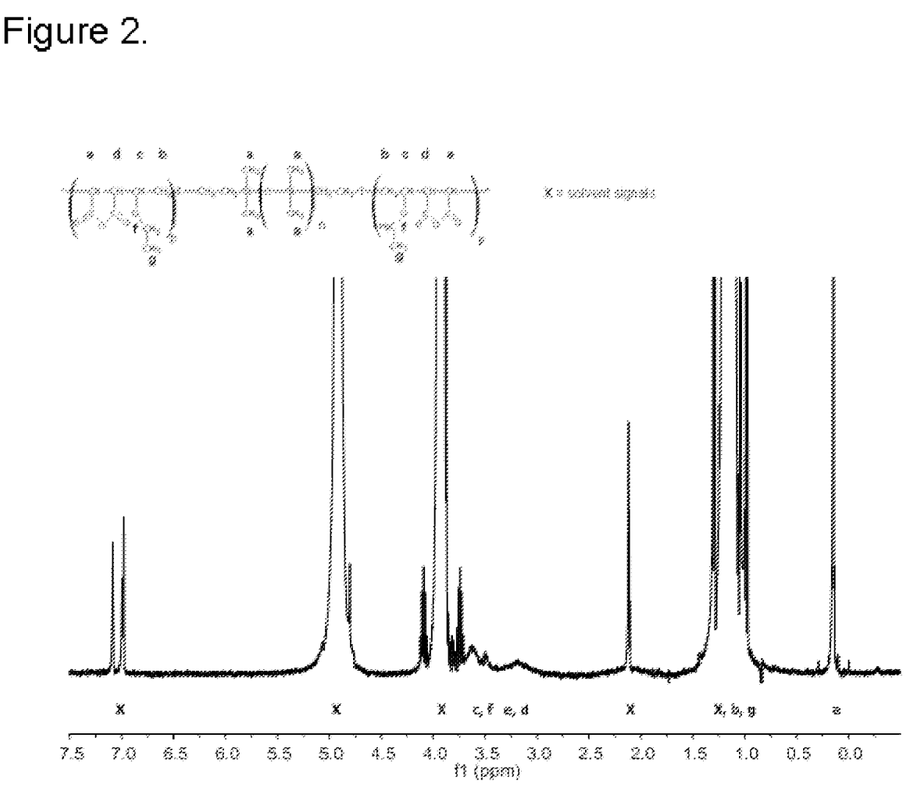
FIG. 2 shows the $^1$H NMR spectrum of PDMS/MA/VEE 2/2/2 terpolymer.
Figure 3:
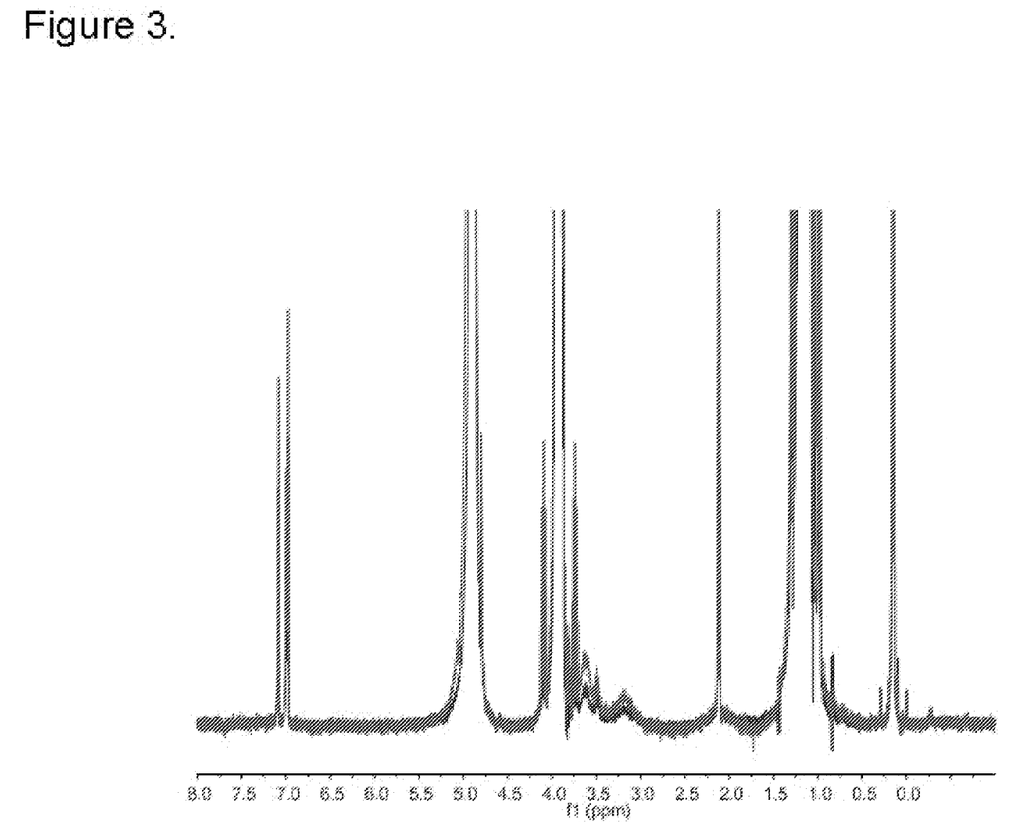
FIG. 3 shows the $^1$H NMR spectra of PDMS/MA/VEE 2/1/1 (maroon) DMS/MA/VEE 2/2/2 (cyan) scaled to have matched PDMS signals at 0.14 ppm.

PDMS = polydimethylsiloxane;
CHO = cyclohexene oxide;
GME = glycidyl methyl ether;
VP = vinyl pyrrolidone;
VA = vinyl acetate;
MA = maleic anhydride;
VEE = vinylethyl ether;
VPEG = vinyl terminated polyethylene oxide;
DOM = dioctyl maleate Characterization of PDMS/VEE/MA Terpolymers FIGS. 1 and 2 show the NMR spectra for the terpolymers. The two terpolymer samples produced similar signals. The large signals at 4.89 ppm, 3.92 ppm, and 1.13 ppm are due to the 2-propanol solvent. The signals at 7.08 ppm, 6.98 ppm, and 2.12 ppm are due to the toluene-$d_8$ solvent. The sharp signal at 0.14 ppm is due to PDMS from the sample material. Software prediction of alternating copolymers of maleic anhydride and vinyl ethyl ether predict signals at 1.1 ppm, 1.6 ppm, and three signals between 3.3 ppm and 3.4 ppm. Any signal present at 1.1 ppm is obscured by the much larger 2-propanol signal. The signal predicted at 1.6 ppm is also not observed, and may also be obscured by the solvent if it is shifted upfield from the prediction. Signals are observed at 3.62 ppm and 3.50 ppm which appear to correspond to the MA/VEE units. There is a broad signal around 3.2 ppm which represents a third and possibly a fourth signal. FIG. 3 shows an overlay of the two spectra, scaled to have the sample PDMS signal intensity to be equal. In this figure, it is clearly shown that the signals between 3.62 ppm and 3.2 ppm are higher in PDMS/MA/VEE 2/2/2 than the 2/1/1 terpolymer which matches expectations based on the stated terpolymer ratios. If it is assumed that the MA/VEE in these samples is an alternating copolymer of maleic anhydride and vinyl ethyl ether, the three signals at 3.62 ppm, 3.50 ppm, and 3.2 ppm are consistent with five protons from the copolymer, and the ratio of MA/VEE to PDMS can be calculated. The results of these calculations are shown in Table 2.

TABLE 2

Composition of terpolymers as determined by $^1$H NMR spectroscopy.

| | Weight % | |
|---|---|---|
| Copolymer description | PDMS | MA/VEE |
| PDMS/MA/VEE 2/1/1 | 63.2 | 36.8 |
| PDMS/MA/VEE 2/2/2 | 43.5 | 56.5 |

Figure 4:
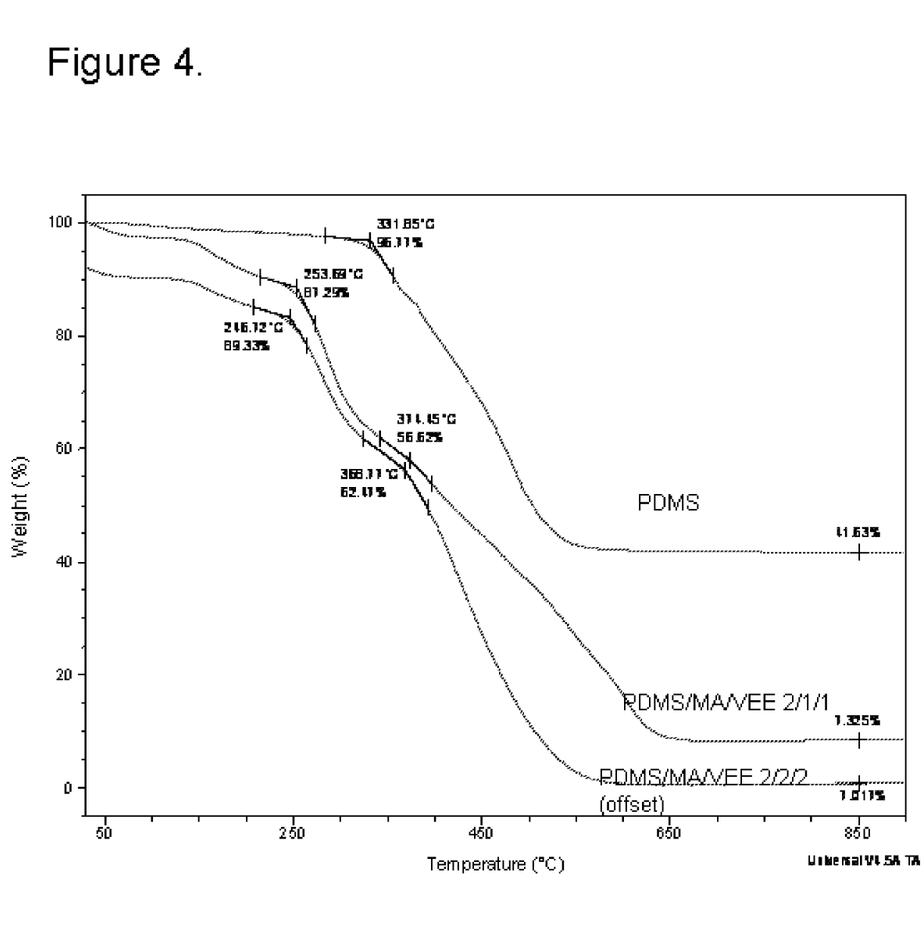
FIG. 4 shows the TGA of PDMS precursor, PDMS/MA/VEE 2/1/1 and 2/2/2 terpolymers.

The TGA of α,ω-hydride-terminated PDMS precursor along with the copolymer samples are shown in FIG. 4. For the precursor, there is a low temperature weight loss accounting for approximately 3% that is likely due to residual monomer or solvent in the oligomer. The major weight loss which starts around 330° C. is due to the degradation of the silicone polymer backbone. There is a significant char left from the PDMS averaging about 38% over three TGA runs. Both terpolymers (2/1/1 and 2/2/2 molar ratios) show four distinct regions—the first one is up to 50° C., the second from 140-250° C., the third from 250-325° C., and the fourth from 325-550° C. The first two regions are probably due to residual solvent and monomers. The nature of the second weight loss is less obvious but could be due to residual toluene (used in the synthesis) with a boiling point of 110° C., residual octamethylcyclotetrasiloxane (D4) with a boiling point of 175° C., or residual maleic anhydride with a boiling point of 202° C. The third and fourth regions are attributed to the terpolymer degradation. The terpolymer compositions show approximately 7% char remaining, which is expected due to the lower level of PDMS as compared to the neat PDMS precursor.

Figure 5:
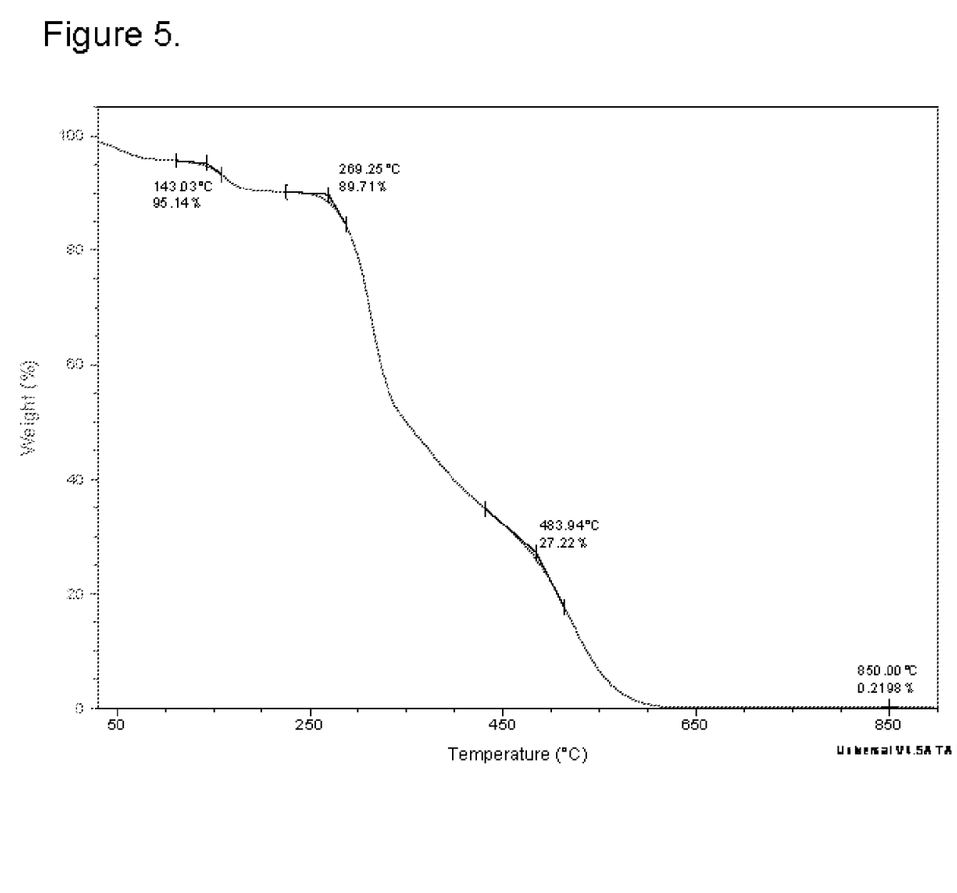
FIG. 5 shows the TGA of Gantrez™ AN-169 (MA/VME copolymer).

Polydimethylsiloxane is known to produce a char in air due to the formation of silica. Most hydrocarbon based compounds will completely oxidize in air and will not leave any residue. To verify this, the commercially available copolymer of maleic anhydride/vinyl methyl ether, Gantrez™ AN-169 (ISP Corporation) was analyzed using the same conditions (see FIG. 5). As expected, this copolymer did not show any char. The degradation profile of the copolymer is consistent with the lower temperature degradation profiles of the terpolymers with four distinct regions. This indicates the presence of vinyl ether and maleic anhydride comonomers in the terpolymer system. As there is no expected charring of the hydrocarbon portions of the terpolymer system, the amount of residue is assumed to be related to the amount of PDMS in the terpolymer. The amount of PDMS in the terpolymer was calculated by taking the ratio of char weight between the terpolymer and the neat precursor. Based on these calculations, the weight percent of PDMS in the terpolymers was calculated to be less than 20% (Table 2), which is considerably lower than expected based on the initial loading in the reactor and from NMR analysis. These differences could be due to an altered charring mechanism of siloxane chain in the presence of the hydrocarbon comonomers.

TABLE 2

TGA results of PDME/MA/VEE terpolymers.

| Polymer Designation | TGA Residue (%) | Weight % PDMS (calculated from TGA residue) | Weight % PDMS expected |
|---|---|---|---|
| α,ω-hydride-terminated PDMS precursor (DMS-H25) | 38* | — | 100 |
| PDMS/MA/VEE 2/1/1 | 7.0 | ~18 | 50 |
| PDMS/MA/VEE 2/2/2 | 7.3 | ~19 | 33 |

*average of 3 runs

Figure 6:
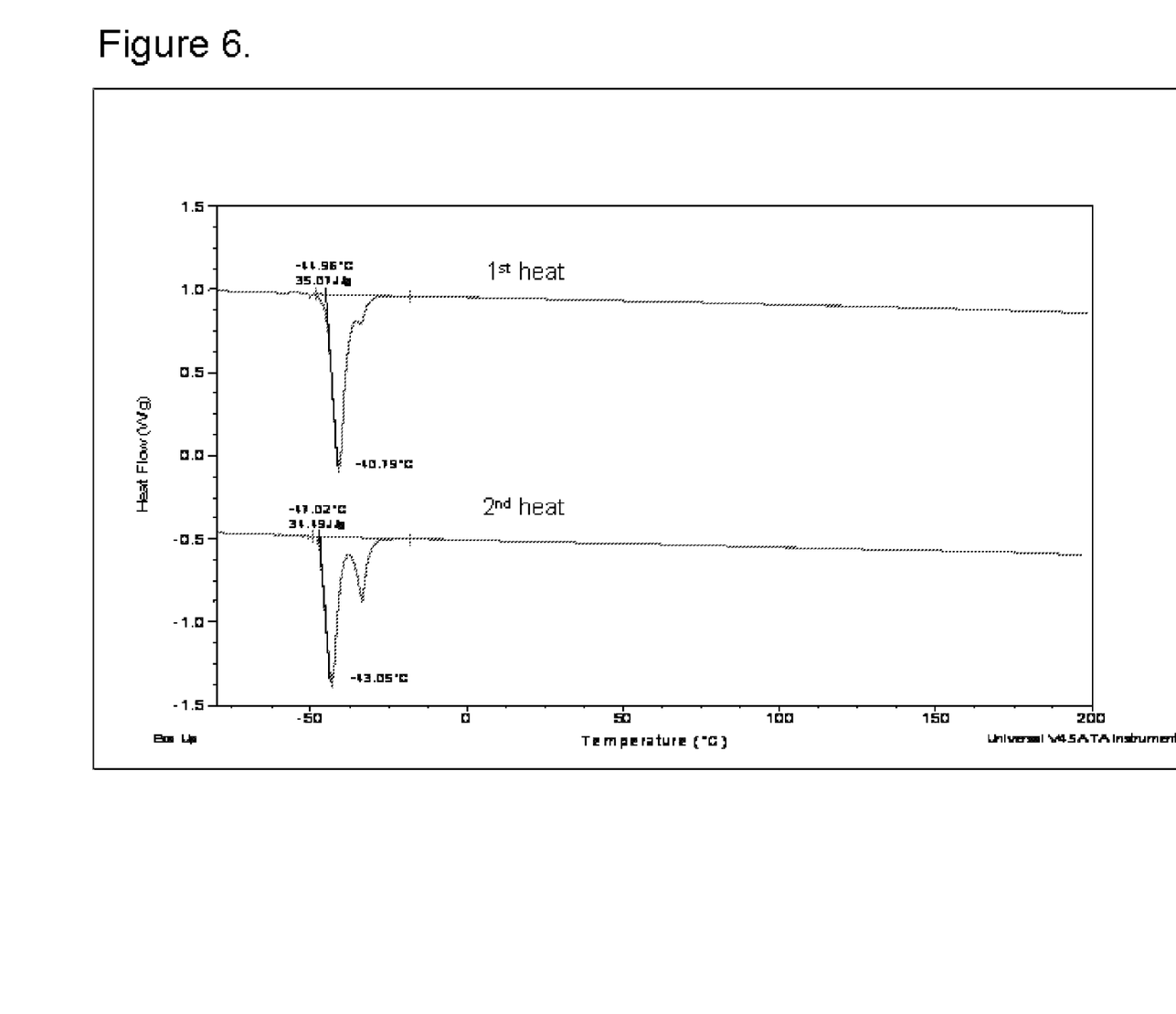
FIG. 6 shows the DSC of a, w-hydride-terminated PDMS precursor (DMS-H25 from Gelest Inc.).
Figure 7:
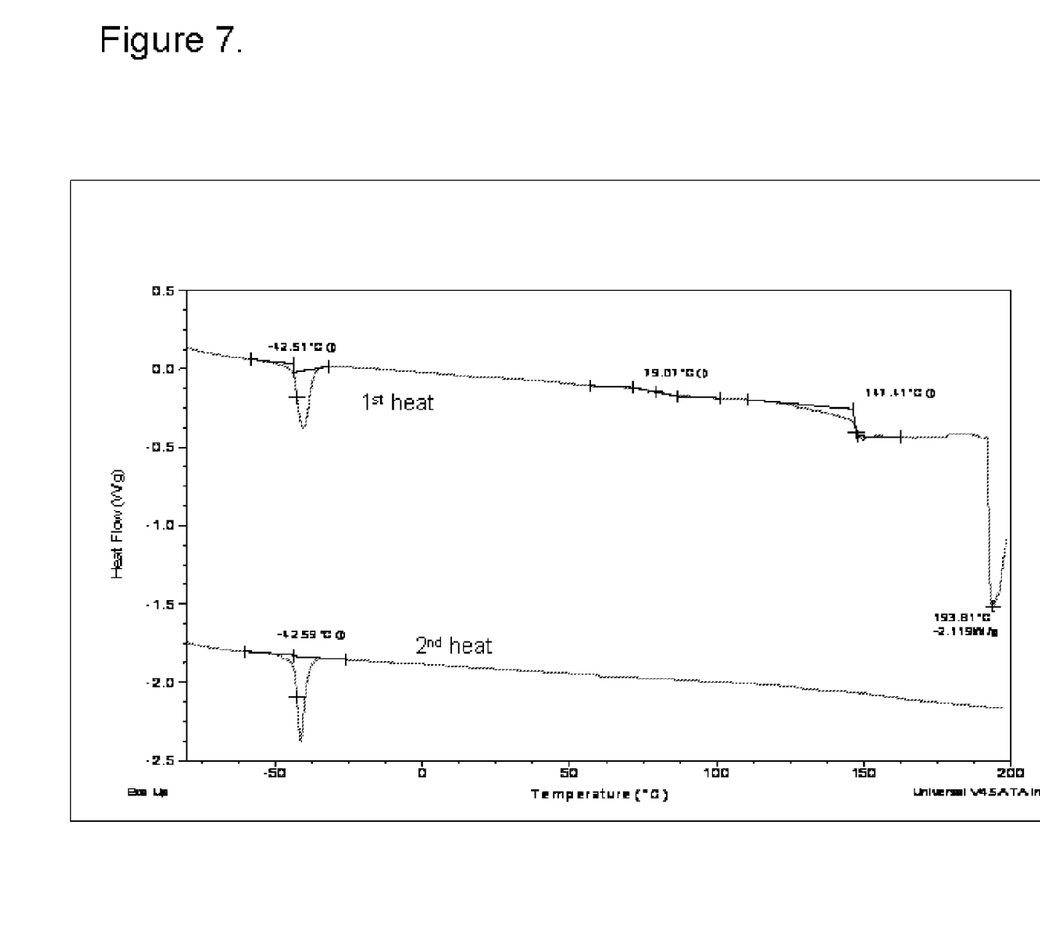
FIG. 7 shows the DSC of PDMS/MA/VEE 2/1/1.
Figure 8:
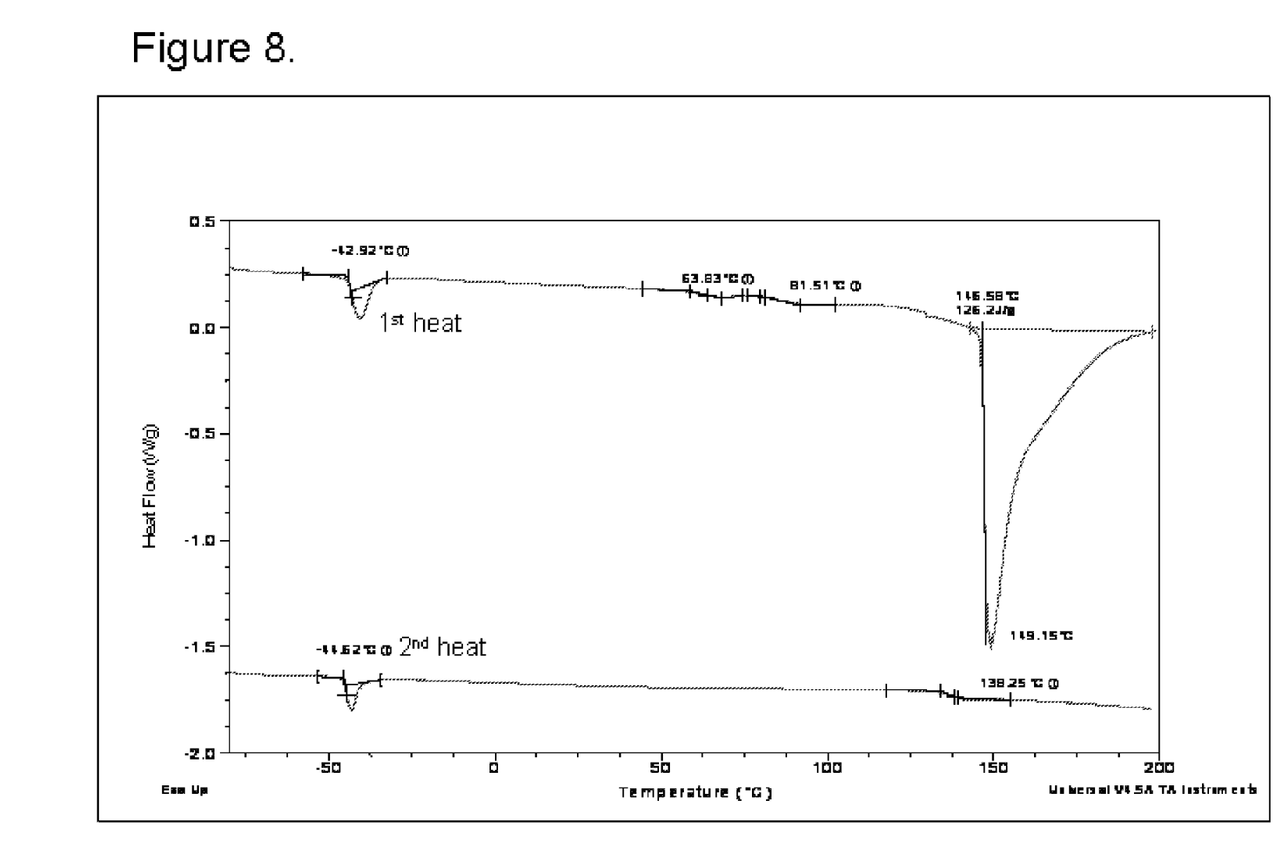
FIG. 8 shows the DSC of PDMS/MA/VEE 2/2/2.
Figure 9:
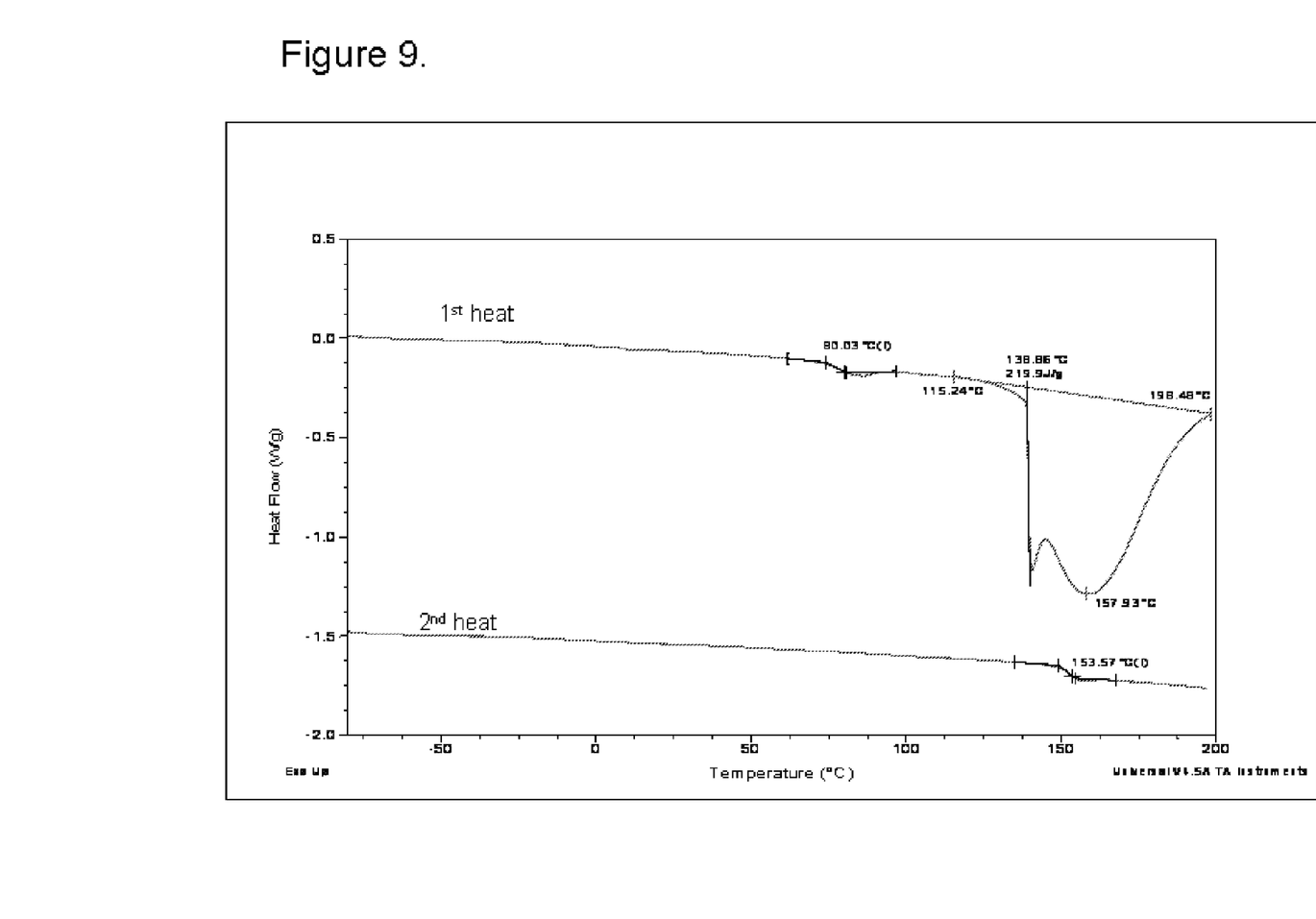
FIG. 9 shows the DSC of Gantrez™ AN-169.

DSC data for the PDMS precursor (DMS-H25 from Gelest) from the first and second runs are shown in FIG. 6. This data shows a significant endotherm in both the first and second heats at around −40° C. which is attributed to the melting temperature of PDMS. FIGS. 7 and 8 are the DSC scans for the two terpolymers PDMS/MA/VEE (2/1/1 and 2/2/2 molar ratios). An endotherm in the same region (−40° C.) can be seen in the terpolymers which indicates the presence of PDMS crystallites in these terpolymers. Each of the terpolymer systems also show a high temperature endotherm in the first heat that is not present in the second heat, indicating that crystallization is not occurring during the cooling cycle in the DSC. This endotherm is from the MA/VEE segments of the terpolymer since this is not present in the precursor but is also seen in Gantrez AN-169 (FIG. 9). Both terpolymer samples exhibit a weak glass transition temperature, $T_g$, between 135° C. and 145° C., which is lower than the reported $T_g$ of 146° C. for poly(MA-alt-VEE)(8). This indicates the presence of at least two distinct phases, a PDMS phase, and an organic phase in the terpolymers. FIG. 9 shows the first and second heat, respectively, of Gantrez AN-169, which is reported to have a $T_g$ of 154° C. according to the supplier literature (ISP corporation).

Figure 10:
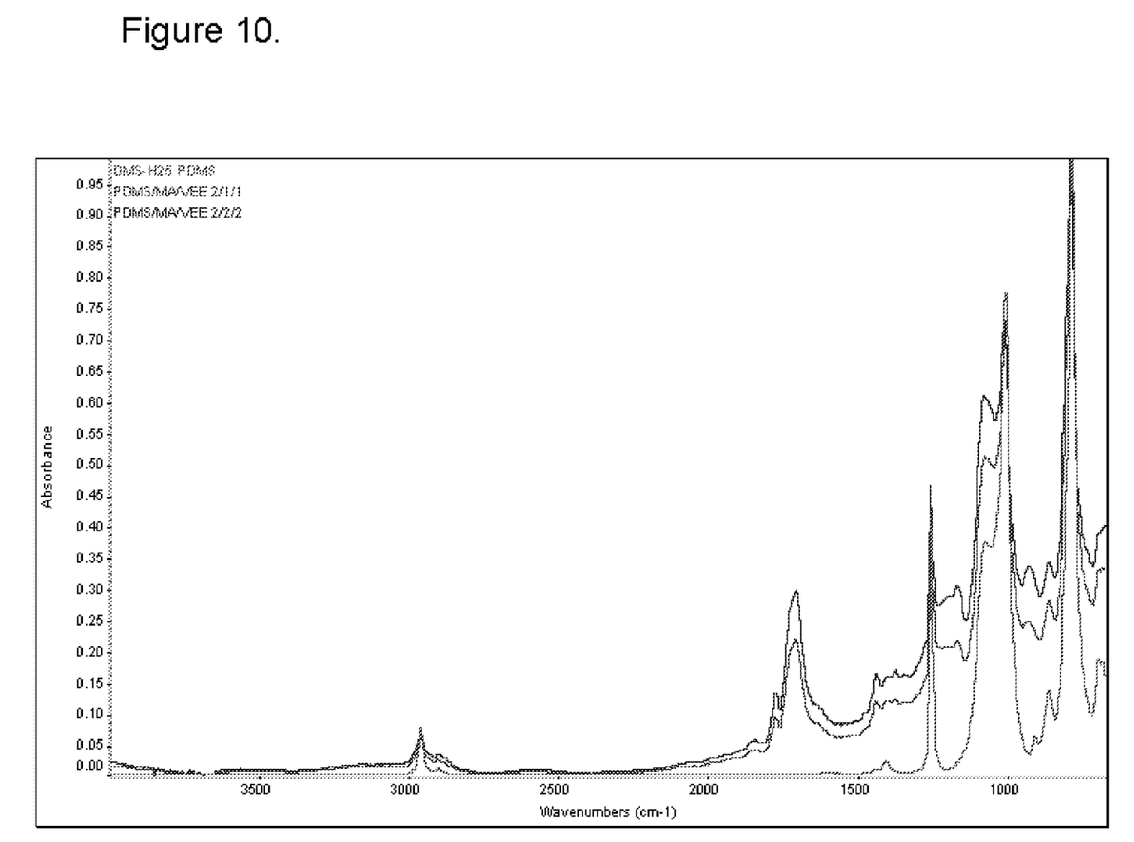
FIG. 10 shows the FTIR of PDMS/MA/VEE terpolymers and PDMS starting material.
Figure 11:
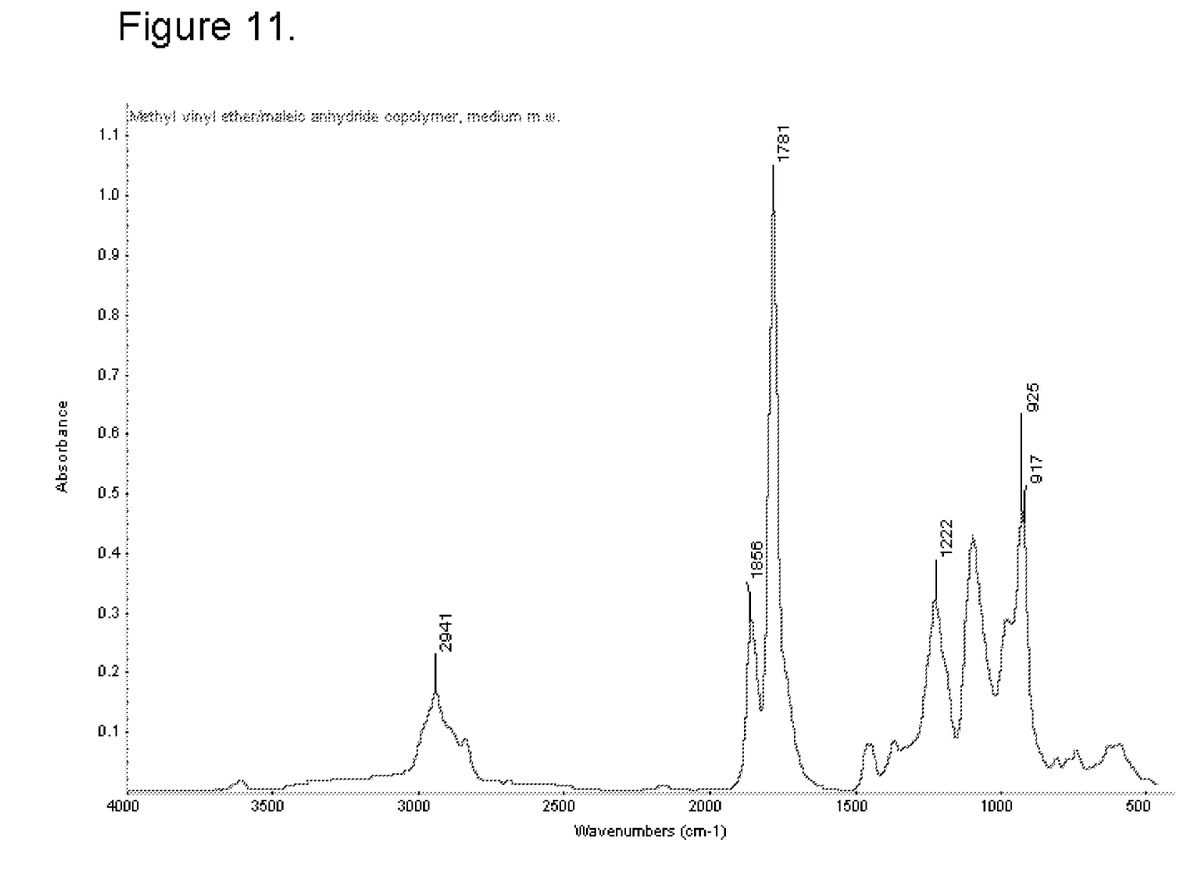
FIG. 11 shows the Reference FTIR of MA/VME Copolymer (Gantrez™ AN-169).

FIG. 10 shows the FTIR spectra for the PDMS/MA/VEE terpolymers overlaid with the PDMS precursor (bottom curve). The precursor shows fingerprint bands at 1258 cm$^{-1}$ (Si—CH$_3$), 1067 cm$^{-1}$ and 1013 cm$^{-1}$ (Si—O—Si stretching vibration), and 793 cm$^{-1}$ (Si—C stretching and CH$_3$ rocking) for PDMS. The terpolymers show distinct bands at 1856 cm$^{-1}$ and 1781 cm$^{-1}$ which can be attributed to anhydride group. A reference spectrum of maleic anhydride/vinyl methyl ether (Gantrez™ AN-169 from ISP corporation) provided in FIG. 11 provides a close match to the terpolymer samples in FIG. 10. This confirms the presence of PDMS and MA/VEE moieties in the copolymers.

Amphiphilic Silicone PSA Properties: Tackiness and Moisture Vapor Transmission Rate (MVTR)

The amphiphilic silicone pressure sensitive adhesive was prepared by blending PDMS/MA/VEE terpolymer into a conventional silicone gel adhesive at 20 wt % loading level, prior to curing the gel. The reactive blend was then coated on a polyurethane film using a Werner-Mathis coater and cured at 150° C. for 3 minutes. The coating thickness was about 10 mils. The moisture vapor transmission rate (MVTR) of the adhesives was measured using the upright cup method ASTM E96-00. Table 3 shows the summary of tackiness and % change in moisture vapor transmission rate compared to neat silicone gel adhesive. The composition with the amphiphilic copolymer additive was still a pressure sensitive adhesive as it was tacky to touch, and the MVTR showed an increase of about 800% compared to the neat silicone gel.

TABLE 3

| Adhesive Composition | % change in MVTR | Tackiness |
|---|---|---|
| Neat silicone gel adhesive | Not applicable | Yes |
| Silicone gel adhesive + 20 wt % PDMS/MAA/VEE copolymer | 800% | Yes |

Amphiphilic silicone terpolymers were synthesized based on a polydimethylsiloxane macroinitiator containing thermolyzable bis(silylpinacolate) groups in the polymer backbone. The terpolymers showed solubility in a toluene/2-propanol mixture but not the individual solvents indicating the presence of covalently bonded hydrophobic and hydrophilic segments. In addition, the mild swelling of the samples in alkali solution further supports the presence of hydrophilic and hydrophobic domains. The presence of both PDMS and MA/VEE components were confirmed by NMR, TGA, DSC and FTIR. Blending these amphiphilic terpolymers into silicone pressure sensitive gel adhesives resulted in an increase in the moisture vapor transmission rate, however, the peel strength also reduced significantly. The adhesion under moist conditions showed a significant improvement with no residue on adhesive removal indicating the terpolymer is not solubilized in moisture.

We believe that this is the first time an amphiphilic silicone terpolymer has been synthesized for pressure sensitive adhesive application with a demonstrated increase in the moisture vapor transmission rate (MVTR). While one could achieve a similar increase in MVTR by blending in hydrophilic polymers, the current approach is superior for two reasons: 1) it is possible to achieve a considerable increase in MVTR with low loading levels of amphiphilic copolymers in the adhesive, and; 2) the amphiphilic copolymer will not leach out of the adhesive in the presence of moisture. In addition, the selection of a hydrolysable monomer such as maleic anhydride, improves the adhesion to skin under moist conditions.

We claim:

1. A pressure sensitive adhesive comprising an amphiphilic terpolymer of polydimethylsiloxane, wherein the terpolymer is prepared using a polydimethylsiloxane macroinitiator and two reactive hydrophilic or amphiphilic monomers, oligomers, macromers, and combinations thereof, wherein the reactive hydrophilic or amphiphilic monomer is selected from a group consisting of vinyl ethers and unsaturated acids or anhydrides and their salts and the reactive hydrophilic or amphiphilic oligomer and macromer has a reactive vinyl group.

2. The pressure sensitive adhesive according to claim 1 comprising an amphiphilic terpolymer of poly(dimethylsiloxane)-poly(maleic anhydride-vinyl ethyl ether) (PDMS/MA/VEE) and a silicone gel adhesive blended together.

3. A medical device comprising a pressure sensitive adhesive comprising an amphiphilic terpolymer of polydimethylsiloxane, wherein the terpolymer is prepared using a polydimethylsiloxane macroinitiator and two reactive hydrophilic or amphiphilic monomers, oligomers, macromers, wherein the reactive hydrophilic or amphiphilic monomer is selected from a group consisting of vinyl ethers and unsaturated acids or anhydrides and their salts, and the reactive hydrophilic or amphiphilic oligomer or macromer has a reactive vinyl group.

4. The pressure sensitive adhesive according to claim 1 wherein the amphiphilic terpolymer of polydimethylsiloxane is poly(dimethylsiloxane)-poly(maleic anhydride-vinyl ethyl ether) (PDMS/MA/VEE), with the molar ratio of macroinitiator to co-monomer in the range of 1/1/1 PDMS/MA/VEE to 2/1/1 PDMS/MA/VEE.

5. The pressure sensitive adhesive according to claim 1 wherein the amphiphilic terpolymer of polydimethylsiloxane is poly(dimethylsiloxane)-poly(maleic anhydride-vinyl ethyl ether) (PDMS/MA/VEE) and the pressure sensitive adhesive has a moisture vapor transmission rate increase of about 800% compared to neat silicone gel adhesive.

6. The pressure sensitive adhesive according to claim 1 wherein the amphiphilic terpolymer of polydimethylsiloxane is poly(dimethylsiloxane)-poly(maleic anhydride-vinyl ethyl ether) (PDMS/MA/VEE) and the pressure sensitive adhesive has reduced peel strength compared to neat silicone gel adhesive.

* * * * *